United States Patent [19]
Collins et al.

[11] Patent Number: 5,209,104
[45] Date of Patent: May 11, 1993

[54] METHOD FOR DESATURATING A POROUS ROCK FOR ELECTRICAL RESISTIVITY MEASUREMENTS

[75] Inventors: Samuel H. Collins, Desoto; Eve S. Sprunt, Farmers Branch, both of Tex.

[73] Assignee: Mobil Oil Corporation, Fairfax, Va.

[21] Appl. No.: 824,268

[22] Filed: Jan. 23, 1992

[51] Int. Cl.[5] .................................................. G01N 15/08
[52] U.S. Cl. ........................................... 73/38; 324/376
[58] Field of Search ........................ 73/38; 324/376, 366

[56] References Cited

U.S. PATENT DOCUMENTS

| | | | |
|---|---|---|---|
| 3,839,899 | 10/1974 | McMillen | 73/38 |
| 4,379,407 | 4/1983 | Masse et al. | 73/579 |
| 4,467,642 | 8/1984 | Givens | 73/152 |
| 4,543,821 | 1/1985 | Davis, Jr. | 73/38 X |
| 4,546,318 | 10/1985 | Bowden | 324/376 |
| 4,686,477 | 8/1987 | Givens et al. | 324/366 |
| 4,688,238 | 8/1987 | Sprunt et al. | 378/4 |
| 4,734,649 | 3/1988 | Barnaby | 324/376 |
| 4,868,751 | 9/1989 | Dogru et al. | 364/422 |
| 4,907,442 | 3/1990 | Jones et al. | 73/38 |
| 4,907,448 | 3/1990 | Givens | 73/38 X |
| 4,926,128 | 5/1990 | Givens | 324/376 |
| 5,069,065 | 1/1991 | Sprunt et al. | 73/38 X |
| 5,079,948 | 1/1992 | Collins et al. | 73/38 X |
| 5,086,643 | 2/1992 | Marek | 73/38 |

FOREIGN PATENT DOCUMENTS

| | | | |
|---|---|---|---|
| 1198414 | 12/1985 | U.S.S.R. | 73/38 |
| 1213388 | 2/1986 | U.S.S.R. | 73/38 |

OTHER PUBLICATIONS

"SCA Guidelines for Sample Preparation and Porosity Measurement of Electrical Resistivity Samples", Maerefat et al., *The Log Analyst,* vol. 31, No. 2, pp. 68–75, Mar.–Apr., 1990.

*Primary Examiner*—Tom Noland
*Assistant Examiner*—Joseph W. Roskos
*Attorney, Agent, or Firm*—Alexander J. McKillop; George W. Hager, Jr.

[57] ABSTRACT

A porous rock is saturated with a first fluid and electrical resistivity is measured along its length. A second fluid, immiscible with the first fluid, is injected into the porous rock at a first flow rate. This injection continues until displacement of the first fluid from the porous rock ceases and the pressure drop along the porous rock becomes constant, indicating a first residual fluid saturation equilibrium. The foregoing is repeated for a plurality of increasing second fluid injection flow rates to effect electrical resistivity measurements at decreasing residual fluid saturation equilibriums. The method may then be repeated substituting the second fluid for the first and vice versa to perform an imbibition experiment.

22 Claims, 1 Drawing Sheet

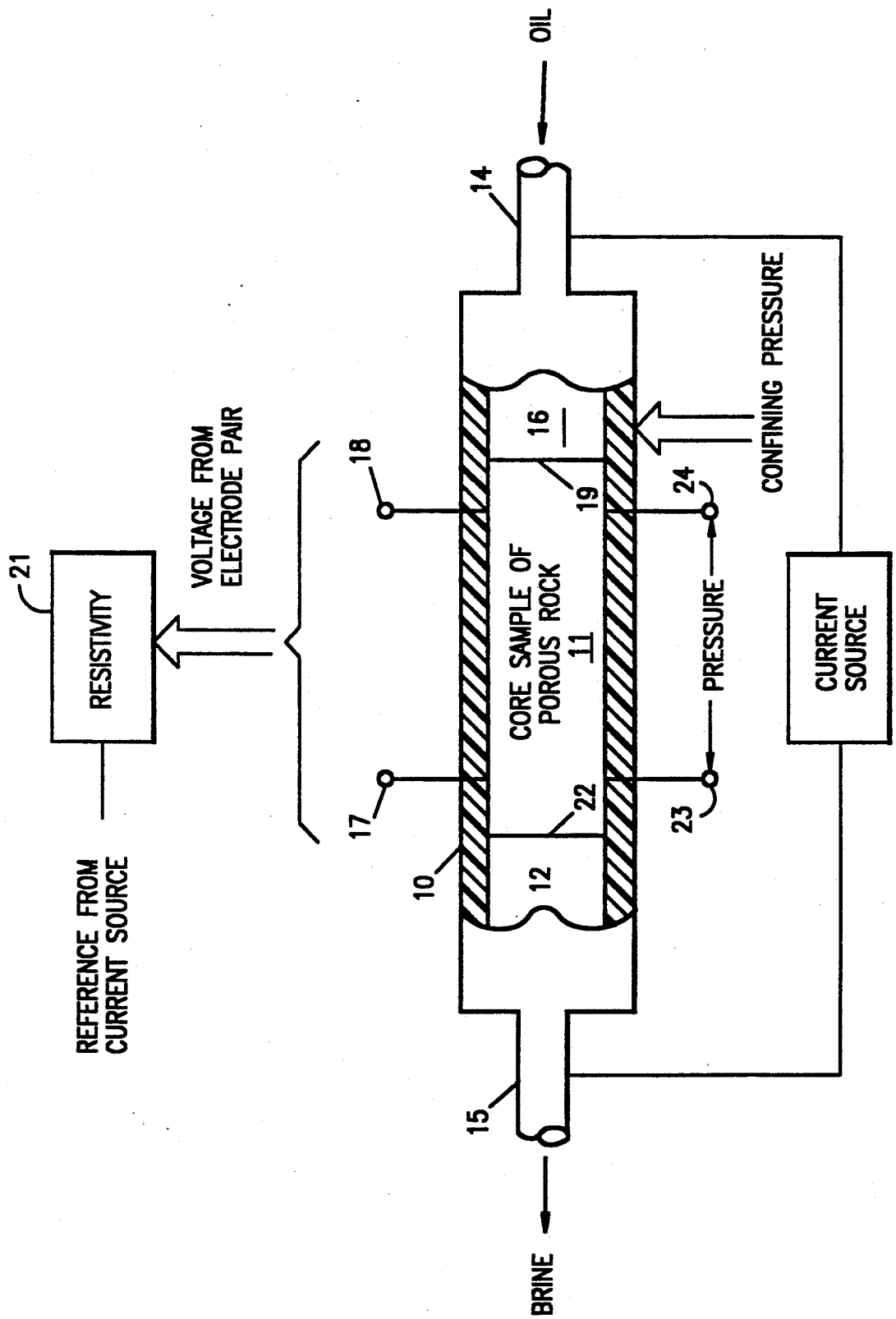

METHOD FOR DESATURATING A POROUS ROCK FOR ELECTRICAL RESISTIVITY MEASUREMENTS

BACKGROUND OF THE INVENTION

This invention relates to the area of oil and natural gas exploration and, more particularly, to a method for identifying regions of rock formations from which hydrocarbons may be produced.

Hydrocarbon saturation $S_o$ is generally determined from a measured water saturation $S_w$ as follows:

$$S_o = 1 - S_w \quad (1)$$

Water saturation present in a subterranean formation is typically determined from interpretation of conventional electrical (i.e., resistivity) logs taken through a borehole drilled through the formation. Water saturation of the available pore space of the formation is determined from the resistivity log measurements using the Archie equation set forth in "The Electrical Resistivity Log As An Aid In Determining Some Reservoir Characteristics", Trans. AIME, Vol. 46, pp. 54–62, 1942, by G. E. Archie. This equation is expressed as follows:

$$S_w{}^n = R_w / \phi^m R_t \quad (2)$$

Where "$S_w$" is the fractional water saturation (i.e. free and bound water of the formation expressed as a percent of the available pore space of the formation), "$R_w$" is the formation water resistivity, "$\phi$" is the formation porosity, "$R_t$" is the formation electrical resistivity, "n" is the saturation exponent and "m" is the porosity or cementation exponent. The Archie equation may be expressed in other ways and there are numerous methods in the art for determining, measuring or otherwise obtaining the various components needed to predict fractional water saturation $S_w$ from the formation resistivity, $R_t$, using the equation in any of its forms.

Archie defined two quantities that provided the basis for his water saturation equation (1). The first quantity is the formation factor F which defines the effect of the rock matrix on the resistivity of water as follows:

$$F = R_o / R_w \quad (3)$$

where
$R_o$ = resistivity of water saturated rock and
$R_w$ = water resistivity.

Archie reasoned that for a given value of $R_w$, the formation factor F would decrease with increasing porosity, $\phi$, to some exponent m:

$$F = 1/\phi^m \quad (4)$$

This porosity exponent m has also become known as the Archie cementation exponent. Thus Archie provided a useful characterization of a rock fully saturated with a conducting brine in terms of the water resistivity $R_w$, porosity $\phi$ and a rock parameter m. It is important to note that Archie assumed all conductance to be in the brine.

The second quantity is the resistivity index I defined as the ratio of the resistivity of a rock partially saturated with water and hydrocarbon, $R_t$, to the same rock saturated fully with water, $R_o$, as follows:

$$I = R_t / R_o \quad (5)$$

Archie reasoned that as the water saturation decreased (i.e. hydrocarbon saturation increased) the resistivity $R_t$ and hence I would increase to some exponent n:

$$I = 1/S_w{}^n \quad (6)$$

where $S_w$ = volume of water in pores/total pore volume. This exponent n has become known as the Archie saturation exponent. It is again important to note that Archie assumed all conductance to be in the brine and further that all pores within the rock have the same water saturation $S_w$.

It is these two equations (4) and (6) for the formation factor F and resistivity index I respectively that Archie combined to provide the water saturation expression $S_w$ of equation (2). Certain logs have provided formation resistivity $R_t$ and porosity $\phi$. Water samples provide the best values for $R_w$. Standard practice is to measure rock sample resistivities $R_o$ and $R_t$ for a number of water saturations and to plot the logarithm of I versus the logarithm of $S_w$. Archie's equations assume such a logarithmic plot is a straight line with slope of $-n$.

To determine the saturation exponent n, electrical resistivity measurements are carried out on core samples of porous rock at differing water saturation conditions. It is highly desirable for these water saturation conditions to be representative of those encountered in the formation. Different methods for desaturating core samples of porous rocks for electrical resistivity measurements are reviewed in "SCA Guidelines for Sample Preparation and Porosity Measurement of Electrical Resistivity Samples" by Maerefat et al., *The Log Analyst*, v.31, n.2, pgs. 68–75, March–April, 1990. One of the desaturating methods described is the one-phase displacement method in which water saturation in a core sample of a porous rock is altered by the injection of a second fluid phase. For example, a core sample may be saturated with conductive brine and oil injected as the displacing phase. This displacement is terminated at different stages, which equate to differing water saturation conditions, and electrical resistivity is measured. The fluids in the core sample are allowed to redistribute (i.e. equilibrate) after injection flow is discontinued before performing the electrical resistivity measurements.

One problem with such a one-phase desaturation method is that the electrical resistivity measurements can suffer from the fluids not redistributing to form a uniform water saturation at each of the differing desired water saturation conditions. also, the electrical resistivity measurements can suffer from capillary end effects due to capillary retention of water at the outflow end of the core sample. The end effect causes a sharp saturation gradient in the core sample, which may in some cases partially dissipate upon cessation of fluid flow. It is therefore an object of the present invention to provide for a one-phase method of desaturating a core sample of a porous rock for electrical resistivity measurements that overcomes such shortcomings of the above described one-phase desaturation method.

SUMMARY OF THE INVENTION

The present invention is directed to a method for desaturating a porous rock for electrical resistivity measurements.

A porous rock is saturated with a first fluid to effect a first fluid saturation throughout said porous rock. Electrical resistivity is measured along a selected length of the first fluid saturated porous rock. A second fluid, immiscible with and of opposite electrical conductance with the first fluid, is injected into the porous rock at a first flow rate to displace a portion of the first fluid from the porous rock and effect a second fluid saturation within the porous rock that is a minimum partial fluid saturation with respect to the first fluid saturation for the first flow rate. The pressure drop across the selected length of porous rock is measured. The injection of the second fluid at the first flow rate is terminated when displacement of the first fluid from the porous rock ceases and the measured pressure drop along the selected length of porous rock is constant, thereby effecting a first residual fluid saturation equilibrium within the porous rock. Electrical resistivity is again measured along the selected length of porous rock at such first residual fluid saturation equilibrium. The foregoing steps are thereafter repeated for each of a plurality of increasing second fluid flow rates to effect decreasing residual fluid saturation equilibriums.

In a further aspect, the first fluid saturation of the porous rock is effected by injecting the first fluid into the porous rock in a first direction and then injecting the first fluid under back pressure in an opposite direction through the porous rock.

In a still further aspect, fluids of opposite conductance to the first fluid with progressively increasing viscosities are used during the repeated second fluid injections to effect decreasing residual fluid saturation equilibriums.

In a yet further aspect, the ratio of the measured pressure drop along the selected length of porous rock to the injected flow rate of the second fluid is determined as a measure of particle migration through the porous rock.

In one embodiment of the invention, a brine is injected into a core sample of a porous rock in a first direction through the core sample and then under back pressure in an opposite direction to effect a complete brine saturation of the core sample. Electrical resistivity is then measured along a selected length of the brine-saturated core sample. Thereafter, oil is injected into the core sample at a first flow rate to displace a portion of the brine from the core sample to effect a brine saturation within the core sample that is a minimum brine saturation with respect to such first oil flow rate. The resulting brine displacement from the core sample by the injected oil is monitored along with the pressure drop along the selected length of core sample. This injection of oil at the first flow rate is terminated when brine displacement from the core sample ceases and the pressure drop along the selected length of core sample becomes constant, thereby indicating a first residual brine saturation equilibrium condition within the porous rock. Electrical resistivity is again measured for this first residual brine saturation equilibrium. The foregoing is thereafter repeated for each of a plurality of increasing oil flow rates to effect decreasing brine saturation equilibriums. In a further aspect, decreasing brine saturation equilibriums can also be effected by injecting progressively increasing viscosities of oil into the core sample for a single or each of a plurality of injection flow rates.

BRIEF DESCRIPTION OF THE DRAWING

The sole drawing illustrates apparatus in which a core sample of a porous rock may be placed in the carrying out of resistivity measurements for a plurality of partial water saturation conditions.

DESCRIPTION OF THE PREFERRED EMBODIMENT

The method of the present invention of desaturating a porous rock through a plurality of partial fluid saturations and making electrical resistivity measurements at each such partial fluid saturation may preferably be carried out with the apparatus shown in the drawing. A pressure sleeve 10, preferably natural or synthetic rubber, is in the form of a cylinder surrounding a core sample 11 of a porous rock to be measured for resistivity at a plurality of fluid saturations. Sleeve 10 is placed inside a suitable pressure vessel (not shown) that can be pressurized up to several thousand pounds per square inch. Typical of such pressure vessels are those described in U.S. Pat. Nos. 3,839,899 to McMillan; 4,688,238 to Sprunt et al; and 4,379,407 to Masse et al. Through such a pressure vessel a pressure is applied to the sleeve 10 and hence to the porous rock 11. A fluid inlet 14 and fluid outlet 15 pass through the end plugs 16 and 12 respectively, which are inserted into the sleeve 10. Both inlet 16 and outlet 12 end plugs also serve as current conducting electrodes for passing current from a source 20 through the porous rock 11 when it contains a sufficient amount of electrically conducting fluid. At least a pair of voltage electrodes 17 and 18 penetrate sleeve 10 and make contact with the porous rock at spaced-apart positions along the length of the porous rock. More than one pair of electrodes may be used.

In carrying out the method of the present invention with such apparatus of the drawing, a core sample of a porous rock 11 is initially fully saturated, preferably with a brine. Such saturation may be effected in several ways, however, one suitable way is to inject the brine through inlet 14 into porous rock 11 and then under back pressure to reverse the injection flow direction through outlet 15 into the porous rock until a full brine saturation of the porous rock is complete. A current is then passed through the porous rock from the current source 20 at this initial brine saturation condition and the voltage V along a selected length L of the porous rock is measured between electrodes 17 and 18. As noted above, the inlet 14 and outlet 15 function as current electrodes conducting current into and out of the porous rock while the brine acts as the conducting medium within the porous rock. Such voltage measurement, as well as later voltage measurements at differing fluid saturations described below, may be carried out in accordance with the teachings of U.S. Pat. Nos. 4,467,642 to Givens; 4,546,318 to Bowden; and 4,686,477 to Givens et al., the teachings of which are incorporated herein by reference. From this voltage V the resistance r of the porous rock along the selected length L is determined using Ohm's Law by the resistance section of the resistivity measuring unit 21. The resistivity measuring unit 21 calculates the resistivity R using the resistance r, the length L and the cross-sectional area A of the core sample of porous rock 11 (e.g. $R = rA/L$).

A non-conducting fluid displacing liquid such as a hydrocarbon, preferably oil, is then injected at a first flow rate through inlet 14 into end 19 of porous rock 11 under a suitable injection pressure. It takes a finite amount of time for the oil to pass through the porous rock displacing the brine through outlet 15. Initially only fingers of oil travel through the porous rock 11 from end 19 toward end 22. This can be thought of as an oil front. There is therefore initially a definite disequilibrium of the brine and oil throughout the porous rock. After an interval of time, such fluid distribution reaches a state of equilibrium throughout the porous rock. The interval of time depends on a number of rock and fluid properties, such as permeability of the rock to brine and oil, length of the core sample of the porous rock, viscosity of the oil, wettability of the sample and pore geometry among others. Such a state of equilibrium is for a minimum partial fluid saturation at the injected flow rate and for the particular viscosity of oil being used and is identified when the pressure drop along the selected length of the porous rock becomes constant. Such a pressure drop can be monitored across pressure taps 23 and 24 by apparatus described and shown in U.S. Pat. No. 4,868,751 to Dogru et al., the teaching of which is incorporated herein by reference. Upon identification of a state of residual fluid saturation equilibrium, electrical resistivity is again measured as described above.

Thereafter, electrical resistivity measurements are carried out for a plurality of decreasing residual fluid saturation equilibriums which are effected by repeating the oil injection step at each of a plurality of increasing oil flow rates. When the injection pressure (i.e. as monitored by the pressure drop along the selected length of porous rock) stabilizes or becomes constant and brine displacement has ceased, the electrical resistivity is again measured.

Different minimum brine saturations can also be effected by repeatedly injecting progressively higher viscosity oils into the porous rock at a single flow rate or for each of the plurality of increasing flow rates for a more complete determination of electrical resistivity.

The ratio of the pressure drop along the selected length of core sample to the flow rate of the displacing oil can be monitored to avoid damaging the core sample of porous rock due to migration of particles within the core sample. If the ratio increases significantly, the measurements should be discontinued.

By carrying out the method of the present invention, the point in time when the plurality of minimum residual fluid saturation equilibriums occur are identified precisely so that electrical resistivity measurements across the selected length of porous rock can be made and used to derive the true value of the saturation exponent for the particular porous rock being examined.

The method of the present invention has been described in conjunction with the above example of a core sample of porous rock saturated with a conducting fluid, such as brine, and a non-conducting displacing fluid, such as oil. This fluid displacement can be referred to as a drainage cycle. However, the method of the present invention can also be carried out by following the drainage cycle during which the electrically conductive fluid saturation progressively decreases, with a second fluid displacement during which the conductive fluid saturation increases. This second fluid displacement can be referred to as an imbibition cycle. Consequently the method of the present invention may be used for measuring fluid distribution equilibrium of two immiscible and oppositely conducting fluids for either a drainage or imbibition cycle, or any repetitive sequencing thereof.

While the foregoing has described a preferred embodiment of the method of the present invention, it is to be understood that various modifications or changes may be made without departing from the spirit and scope of the invention as set forth in the appended claims.

We claim:

1. A method for desaturating a porous rock for electrical resistivity measurements, comprising the steps of:
    a) saturating a porous rock with a first fluid to effect a first fluid saturation throughout said porous rock,
    b) measuring electrical resistivity along a selected length of said first fluid saturated porous rock,
    c) injecting a second fluid which is immiscible with and of opposite electrical conductance with said first fluid into said porous rock at a first flow rate to displace a portion of said first fluid from said porous rock and effect a second fluid saturation within said porous rock that is a minimum partial fluid saturation with respect to said first fluid saturation for said first flow rate,
    d) measuring pressure drop across a selected length of said porous rock,
    e) terminating the injection of said second fluid at said first flow rate when displacement of said first fluid from said porous rock ceases and the measured pressure drop along the selected length of said porous rock is constant, thereby effecting a first residual fluid saturation equilibrium within said porous rock,
    f) measuring electrical resistivity along said selected length of porous rock at said first residual fluid saturation equilibrium, and
    g) repeating steps c) - f) for each of a plurality of increasing second fluid flow rates to effect decreasing residual fluid saturation equilibriums.

2. The method of claim 1 wherein said step of saturating said porous rock with said first fluid to effect said first fluid saturation comprises the steps of:
    a) injecting said first fluid into said porous rock in a first flow direction through said porous rock, and
    b) injecting said first fluid into said porous rock under back pressure in an opposite flow direction to said first flow direction through said porous rock.

3. The method of claim 1 further comprising the step of repeating steps c) - g) with progressively increasing viscosities for said second fluid.

4. The method of claim 1 wherein said first fluid saturation is a complete saturation of said porous rock.

5. The method of claim 1 further comprising the step of determining the ratio of the measured pressure drop along the selected length of porous rock in step d) to the injected flow rate of said second fluid in step c) as a measure of particle migration through said porous rock.

6. The method of claim 1 wherein said steps are carried out under a confining pressure on said porous rock.

7. The method of claim 1 wherein said steps are carried out on a homogeneous porous rock.

8. The method of claim 1 wherein said first fluid is brine.

9. The method of claim 1 wherein said second fluid is a hydrocarbon.

10. The method of claim 9 wherein said second fluid is oil.

11. The method of claim 10 wherein steps c) – g) of claim 1 are carried out for progressively increasing viscosities of oil.

12. The method of claim 9 wherein said second fluid is gas.

13. The method of claim 1 further comprising the step of repeating steps c) – g) with said first fluid being the injecting fluid in place of said second fluid and said second fluid being the displaced fluid in place of said first fluid, thereby effecting an imbibition cycle of fluid displacement.

14. A method for desaturating a porous rock for electrical resistivity measurements, comprising the steps of:
 a) saturating a porous rock with a first fluid to effect a first fluid saturation throughout said porous rock,
 b) measuring electrical resistivity along a selected length of said first fluid saturated porous rock,
 c) injecting a second fluid which is immiscible with and of opposite electrical conductance with said first fluid into said porous rock at a first flow rate to displace a portion of said first fluid from said porous rock and effect a second fluid saturation within said porous rock that is a minimum partial fluid saturation with respect to said first fluid saturation for said first flow rate,
 d) measuring pressure drop across a selected length of said porous rock,
 e) terminating the injection of said second fluid at said first flow rate when displacement of said first fluid from said porous rock ceases and the measured pressure drop along the selected length of said porous rock is constant, thereby effecting a first residual fluid saturation equilibrium within said porous rock,
 f) measuring electrical resistivity along said selected length of porous rock at said first residual fluid saturation equilibrium, and
 g) repeating steps c) – f) with progressively increasing viscosities for said second fluid to effect decreasing residual fluid saturation equilibriums.

15. The method of claim 14 further comprising the step of repeating steps c) – g) for each of a plurality of increasing second fluid flow rates to effect decreasing residual fluid saturation equilibriums.

16. The method of claim 14 further comprising the step of repeating steps c) – g) with said first fluid being the injecting fluid in place of said second fluid and said second fluid being the displaced fluid in place of said first fluid, thereby effecting an imbibition cycle of fluid displacement.

17. A method for desaturating a porous rock for electrical resistivity measurements, comprising the steps of:
 a) injecting a brine into a porous rock in a first direction through said porous rock,
 b) injecting said brine into said porous rock under back pressure in an opposite flow direction to said first flow direction to effect a brine saturation throughout said porous rock,
 c) measuring the electrical resistivity along a selected length of said brine-saturated porous rock,
 d) injecting an oil into said porous rock at a first flow rate to displace a portion of said brine from said porous rock and effect a brine saturation within said porous rock that is a minimum brine saturation with respect to said first oil flow rate,
 e) monitoring the displacement of brine from said porous rock,
 f) measuring pressure drop across a selected length of said porous rock,
 g) terminating the injection of oil at said first flow rate when the displacement of brine from said porous rock ceases and the pressure drop along the selected length of said porous rock is constant, thereby effecting a first residual brine saturation equilibrium within said porous rock,
 h) measuring electrical resistivity along said selected length of said porous rock at said first residual brine saturation equilibrium,
 i) repeating steps d) – h) for each of a plurality of increasing oil flow rates to effect decreasing brine saturation equilibriums.

18. The method of claim 15 further comprising the step of repeating steps b) – i) with progressively increasing viscosities for said oil to effect decreasing brine saturation equilibriums.

19. The method of claim 17 further comprising the step of repeating steps c) – g) with said first fluid being the injecting fluid in place of said second fluid and said second fluid being the displaced fluid in place of said first fluid, thereby effecting an imbibition cycle of fluid displacement.

20. A method for desaturating a porous rock for electrical resistivity measurements, comprising the steps of:
 a) injecting a brine into a porous rock in a first direction through said porous rock,
 b) injecting said brine into said porous rock under back pressure in an opposite flow direction to said first flow direction to effect a brine saturation throughout said porous rock,
 c) measuring the electrical resistivity along a selected length of said brine-saturated porous rock,
 d) injecting an oil into said porous rock at a first flow rate to displace a portion of said brine from said porous rock and effect a brine saturation within said porous rock that is a minimum brine saturation with respect to said first oil flow rate,
 e) monitoring the displacement of brine from said porous rock,
 f) measuring pressure drop across a selected length of said porous rock,
 g) terminating the injection of oil at said first flow rate when the displacement of brine from said porous rock ceases and the pressure drop along the selected length of said porous rock is constant, thereby effecting a first residual brine saturation equilibrium within said porous rock,
 h) measuring electrical resistivity along said selected length of said porous rock at said first residual brine saturation equilibrium,
 i) repeating steps d) – h) with progressively increasing viscosities for said oil to effect decreasing brine saturation equilibriums.

21. The method of claim 20 further comprising the step of repeating steps b) – h) for each of a plurality of increasing oil flow rates to effect decreasing brine saturation equilibriums.

22. The method of claim 20 further comprising the step of repeating steps c) – g) with said first fluid being the injecting fluid in place of said second fluid and said second fluid being the displaced fluid in place of said first fluid, thereby effecting an imbibition cycle of fluid displacement.

* * * * *